United States Patent [19]

Schmidt

[11] Patent Number: 5,401,528
[45] Date of Patent: Mar. 28, 1995

[54] USE OF COMPOSITIONS BASED ON ORGANICALLY MODIFIED SILICIC ACID POLYCONDENSATES FOR COATING TEETH AND DENTAL PROSTHESES

[75] Inventor: Monika Schmidt, Jena-Winzerla, Germany

[73] Assignee: Thera Patent GmbH & Co. KG Gesellschaft für industrielle Schutzrechte, Seefeld, Germany

[21] Appl. No.: 946,372
[22] PCT Filed: Mar. 19, 1992
[86] PCT No.: PCT/EP92/00604
  § 371 Date: Nov. 19, 1992
  § 102(e) Date: Nov. 19, 1992
[87] PCT Pub. No.: WO92/16183
  PCT Pub. Date: Oct. 1, 1992

[30] Foreign Application Priority Data

Mar. 19, 1991 [DE] Germany ............ 9103321 U

[51] Int. Cl.⁶ .................................. A61K 6/00
[52] U.S. Cl. ........................... 427/2.26; 433/217.1
[58] Field of Search ............... 427/2, 2.26; 106/35; 433/215, 217.1, 226

[56] References Cited

U.S. PATENT DOCUMENTS

| | | | |
|---|---|---|---|
| 4,161,518 | 7/1979 | Wen et al. | 424/52 |
| 4,243,658 | 1/1981 | Chang | 424/52 |
| 4,243,692 | 1/1981 | Scholze et al. | 427/2 |
| 4,504,231 | 3/1985 | Koblitz et al. | 433/228 |
| 5,078,988 | 1/1992 | Lin et al. | 424/49 |
| 5,112,640 | 5/1992 | Warunek et al. | 427/2 |
| 5,112,884 | 5/1992 | Hanke | 523/116 |
| 5,132,337 | 7/1992 | Panster et al. | 523/117 |

FOREIGN PATENT DOCUMENTS

| | | |
|---|---|---|
| 2015083 | 10/1990 | Canada. |
| 0078548 | 5/1983 | European Pat. Off.. |
| 0358011 | 3/1990 | European Pat. Off.. |
| 0394797 | 10/1990 | European Pat. Off.. |
| 2051842 | 1/1981 | United Kingdom. |
| 2058088 | 4/1981 | United Kingdom. |

OTHER PUBLICATIONS

Patent Abstract of Japan; vol. 004, No. 159 (C-030), Nov. 6, 1990 & JP, A, 55 105 608 (Takeuchi Mitsuhara) Aug. 13, 1980.

Primary Examiner—Shrive Beck
Assistant Examiner—Erma Cameron
Attorney, Agent, or Firm—Birch, Stewart, Kolasch & Birch

[57] ABSTRACT

Compositions are used for coating teeth and dental prostheses based on a mixture of
(a) at least one compound that is soluble in the reaction medium having the formula (I)

$$MR_x \qquad (I)$$

in which M means Ti, Zr, Si, Ge, Sn or Al, R means halogen, hydroxy, alkoxy, acyloxy or a chelate ligand, and x means the valency of M, and
(b) an organic silane having the formula (II)

$$R''_n SiX_{4-n} \qquad (II)$$

in which R'' means alkyl, alkenyl, aryl, arylalkyl, alkylaryl, arylalkenyl or alkenylaryl, where said radicals may be interrupted by oxygen or sulfur atoms or —NH— groups, X means hydrogen, halogen, hydroxy, alkoxy, acyloxy or the group —NR$_2$' (R'=hydrogen and/or alkyl) and n has the value 1, 2 or 3, and/or
(c) an organofunctional silane having the formula (III)

$$R_m''(R'''Y)_n SiX_{(4-m-n)} \qquad (III),$$

in which R'', X and n have the meaning given above, R''' means alkylene, phenylene, alkylene phenylene or alkenylene, where said radicals may be interrupted by oxygen or sulfur atoms or —NH— groups, Y means halogen atoms, hydroxy, mercapto, polyol, e.g., glycyl or glyceryl, optionally substituted amino, quaternary ammonium, amide, polyamide, aldehyde, keto, carboxy, carboxylic acid alkyl ester, sulfonic acid, phosphoric acid, epoxy, acryloxy or methacryloxy groups and m has the value 1, 2 or 3.

The coatings are resistant to plaque deposits.

30 Claims, No Drawings

USE OF COMPOSITIONS BASED ON ORGANICALLY MODIFIED SILICIC ACID POLYCONDENSATES FOR COATING TEETH AND DENTAL PROSTHESES

The invention relates to the use of compositions based on organically modified silicic acid polycondensates for coating teeth and dental prostheses.

Teeth, and dental prostheses produced from a variety of different materials are subject to the risk of plaque deposits.

The aim of the invention is to protect teeth and dental prostheses from plaque deposits.

According to the invention, said aim is achieved by the use of compositions based on organically modified silicic acid polycondensates. Said compositions are deposited on the teeth or dental prostheses and cured. Adhesion is extraordinarily good; an adhesion promoter is not required.

Surprisingly, it has become apparent that compositions based on organically modified silicic acid polycondensates, after curing, give coatings on the teeth and the dental prostheses that are resistant to plaque deposits. This is surprising because silicic acid polycondensate compositions are described in German patent 27 58 414 as coatings of support materials, e.g., glass vessels for the culture of tissue and cell cultures.

It is stated in column 3, lines 32 ff of said patent that the cells are bound firmly to the substrate in this case—presumably by chemical bonding forces—so that growth in the cell system is guaranteed. Consequently, it should have been expected that coatings based on silicic acid polycondensate are completely unsuitable for the present purposes.

The compositions to be used according to the invention based on organically modified silicic acid polycondensates comprise (a) at least one compound that is soluble in the reaction medium having the formula (I)

$$MR_x \qquad (I)$$

in which M means Ti, Zr, Si, Ge, Sn or Al, R means halogen, hydroxy, alkoxy, acyloxy or a chelate ligand, and x means the valency of M, and (b) an organic silane having the formula (II)

$$R''_n SiX_{4-n} \qquad (II)$$

in which R'' means alkyl, alkenyl, aryl, arylalkyl, alkylaryl, arylalkenyl or alkenylaryl, where said radicals may be interrupted by oxygen or sulfur atoms or —NH— groups, X means hydrogen, halogen, hydroxy, alkoxy, acyloxy or the group —NR$_2$' (R'=hydrogen and/or alkyl) and n has the value 1, 2 or 3, and/or (c) an organofunctional silane having the formula (III)

$$R_m''(R'''Y)_n SiX_{(4-m-n)} \qquad (III),$$

in which R'', X and n have the meaning given above, R''' means alkylene, phenylene, alkylene phenylene or alkenylene, where said radicals may be interrupted by oxygen or sulfur atoms or —NH— groups, Y means halogen atoms, hydroxy, mercapto, polyol, e.g., glycyl or glyceryl, optionally substituted amino, quaternary ammonium, amide, polyamide, aldehyde, keto, carboxy, carboxylic acid alkylester, sulfonic acid, phosphoric acid, epoxy, acryloxy or methacryloxy groups and m has the value 0, 1 or 2.

The compositions may optionally contain another component (d):

(d) sparingly volatile oxides, soluble in the reaction medium, of an element of the main groups Ia to Va or of the sub-groups IVb or Vb of the Periodic System, with the exception of titanium, zirconium, silicon, germanium, tin and aluminum, or compounds of one of said elements that are soluble in the reaction medium and form a sparingly volatile oxide under the reaction conditions.

Compositions containing the components (a), (b) and (c) and optionally (d) are known from European patent 78 548. The entire disclosed content thereof should be included here.

In the above-mentioned formulae (I), (II) and (III), radicals R, R', R'', R''', X or Y present several times may each have the same or a different meaning in one compound.

The alkyl radicals mean, e.g., straight-chain, branched or cyclic radicals with 1 to 20, preferably 1 to 10 carbon atoms and in particular low alkyl radicals with 1 to 6, preferably 1 to 4 carbon atoms. Special examples are methyl, ethyl, n-propyl, isopropyl, n-butyl, sec-butyl, tert-butyl, pentyl, n-hexyl and cyclohexyl. The aryl radicals contain e.g., 6 to 25, preferably 6 to 14 and in particular 6 to 10 carbon atoms. Special examples are phenyl and naphthyl, phenyl being preferred.

The alkenyl radicals are e.g., straight-chain, branched or cyclic radicals with 2 to 20, preferably 2 to 10 carbon atoms and in particular low alkenyl radicals, such as vinyl, allyl and 2-butenyl.

The alkoxy, acyloxy, alkylamino, arylalkyl, alkylaryl, arylalkenyl, alkenylaryl, alkylene, alkylene phenylene, keto, carboxylic acid alkyl ester and substituted amino radicals are derived e.g., from the above-mentioned alkyl, alkenyl and aryl radicals. Special examples are methoxy, ethoxy, n- and i-propoxy, n-, sec- and tert-butoxy, acetyloxy, propionyloxy, monomethylamino, monoethylamino, dimethylamino, diethylamino, monomethylanilino, benzyl, tolyl, methylene, ethylene, dimethylene, toluylene and styryl.

The radicals mentioned may optionally bear customary substituents e.g., halogen atoms, lower alkyl radicals, hydroxy, nitro or amino groups.

Amongst the halogens, fluorine, chlorine and bromine are preferred and chlorine is particularly preferred.

Special examples of titanium or zirconium compounds of component (a) are TiCl$_4$, ZrCl$_4$, Ti(OC$_2$H$_5$)$_4$, Ti(Oi—C$_3$H$_7$)$_4$, Ti(OC$_4$H$_9$)$_4$, Ti(cresyl)$_4$, Zr(OC$_3$H$_7$)$_4$, Zr(OC$_4$H$_9$)$_4$, Ti(acetylacetonato)$_2$(Oi—C$_3$H$_7$)$_2$, Zr(acetylacetonato)$_4$ and other titanium or zirconium complexes with chelate ligands which are preferably coordinated via oxygen and/or nitrogen. Special examples of silicon, germanium, tin and aluminum compounds of component (a) are Si(OH)$_4$, Si(OC$_2$H$_5$)$_4$, Si(OCH$_3$)$_4$, Si(OC$_4$H$_9$)$_4$, Si(OC$_3$H$_7$)$_4$, SiCl$_4$, GeCl$_4$, Ge(OC$_2$H$_5$)$_4$, Sn(OC$_2$H$_5$)$_4$, AlCl$_3$, Al(OC$_2$H$_5$)$_3$, Al(OC$_3$H$_7$)$_4$, Al(OC$_4$H$_9$)$_3$, Al(OH)$_3$.

Preferred organic silanes (b) are e.g.:
(CH$_3$)$_2$—Si—Cl$_2$, (CH$_3$)$_2$—Si—(OCH$_3$)$_2$, (CH$_3$)$_2$—Si—(OC$_2$H$_5$)$_2$, (C$_6$H$_5$)$_2$—Si—Cl$_2$, (C$_6$H$_5$)$_2$—Si—(OC$_2$H$_5$)$_2$, CH$_2$=CH—Si—Cl$_3$, CH$_2$=CH—CH$_2$—Si—(OC$_2$H$_5$)$_3$, CH$_2$=CH—CH$_2$—Si—(CH- $_3COO)_3$, (i—$C_3H_7)_3$—Si—OH, $(CH_3)_2$—Si—$(OH)_2$ and $(C_6H_5)_2$—Si—$(OH)_2$.

Said silanes are in some cases commercial products or they can be prepared according to known methods; compare W. Noll, "Chemie und Technologie der Silicone", Verlag Chemie GmbH, Weinheim/Bergstrasse (1968).

In the organofunctional silanes (c), the bridge group R''' may optionally be interrupted by oxygen or sulfur atoms or —NH— groups. Preferably, 2 to 10 repeating structural units are formed in this manner.

Preferred organofunctional silanes are e.g.:
$(C_2H_5O)_3$—Si—$(CH_2)_3$—OH, $(C_2H_5O)_3$—Si—$CH_2$—$NH_2$, $(CH_3O)_3$—Si—$(CH_2)_2$—NH—$(CH_2)_2$—$NH_2$, $(C_2H_5O)_3$—Si—p—$C_6H_4$—$NH_2$, $(C_2H_5O)_3$—Si—$(CH_2)_3$—OH, $(CH_3O)_3$—Si—$(CH_2)_4$—SH, $CH_3(CH_3O)_2$—Si—$CH_2$—$CH(CH_3)$—$CH_2$—NH—$(CH_2)_2$—$NH_2$, $CH_3(C_2H_5O)_2$—Si—$(CH_2)_4$—$NH_2$, $(CH_3)_2C_2H_5O$—Si—$CH_2$—$NH_2$, $CH_3(C_2H_5O)_2$—Si—$CH_2$—OH, $(CH_3—CH_2—O)_3$—Si—$CH_2$—$CH(CH_3)$—$CH_2$—NH—$(CH_2)_2$—$NH_2$, $(CH_3—CH_2—CH_2—O)_3$—Si—$(CH_2)_4$—$NH_2$, $(C(CH_3)_2(C_2H_5)O)_3$—Si—$CH_2$—$NH_2$

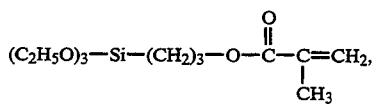

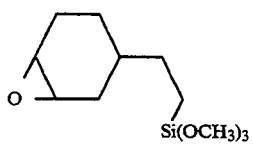

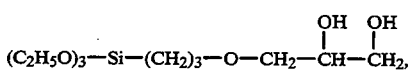

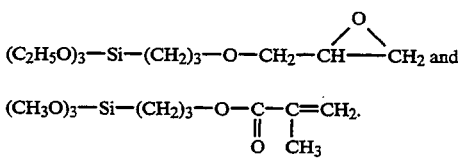

$(CH_3O)_3$—Si—$(CH_2)_3$—O—C—C=$CH_2$.
                                ‖  |
                                O  $CH_3$

In the organic silanes (b) and the organofunctional silanes (c), m preferably has the value 0 and n preferably has the value 1 or 2.

Instead of monomeric starting silanes (b) and (c), pre-condensed oligomers of said silanes, soluble in the reaction medium, may also optionally be used; i.e., straight-chain or cyclic, low molecular weight partial condensates (polyorganosiloxanes) with a degree of condensation of e.g. about 2 to 6.

Sparingly volatile oxides, soluble in the reaction medium, of elements of the main groups Ia to Va or of the sub-groups IVb or Vb of the Periodic System or compounds of said elements forming such sparingly volatile oxides are used as component (d). Component (d) is derived preferably from the following elements: Li, Na, K, Mg, Ca, B, Pb, P, As and/or V, where Na, Ca, Mg, Sr, B and P are particularly preferred.

Amongst the sparingly volatile oxides, $Li_2O$, $Na_2O$, $K_2O$, CaO, MgO, $As_2O_3$, $P_2O_5$ and $B_2O_3$ are particularly preferred.

Compounds that are soluble in the reaction medium and form sparingly volatile oxides are e.g., inorganic acids such as phosphoric acid and boric acid, and esters thereof. Moreover, e.g., halides such as $SiCl_4$ and $HSiCl_3$ and alkoxides such as NaOR, KOR, $Ca(OR)_2$ are suitable, R being derived from low alcohols such as methanol, ethanol, propanol or butanol. Other starting compounds that can be used are corresponding salts with volatile acids, e.g., acetates, basic acetates such as basic lead acetate, and formates.

The compositions contain 1 to 99, preferably 20 to 90, particularly 40 to 80 mole % of component (a) and accordingly 1 to 99, preferably 10 to 80 and particularly 20 to 60 mole % of component (b), or the compositions contain 1 to 99, preferably 20 to 90, particularly 40 to 60 mole % of component (a) and accordingly 1 to 99, preferably 10 to 80 and particularly 20 to 60 mole % of component (c), or the compositions contain 1 to 98, preferably 20 to 80, particularly 40 to 60 mole % of component (a), 1 to 98, preferably 10 to 75 and particularly 15 to 50 mole % of component (b) and 1 to 40, preferably 5 to 30 and particularly 10 to 25 mole % of component (c).

If component (d) is used, the compositions contain 0.1 to 50, preferably 0.5 to 30 and particularly 2 to 20% by wt. of component (d), based on the total weight of the starting components (a) to (d).

The preferably non-aqueous starting components are initially precondensed in the desired quantity ratio, optionally in the presence of a non-aqueous organic solvent and optionally in the presence of a non-aqueous condensation catalyst. Examples of suitable solvents are alcohols, preferably low alcohols such as methanol, ethanol or butanol, ethers, preferably low dialkyl ethers such as diethyl ether or dioxane, ketones e.g., acetone, esters, benzene and mixtures thereof. The amount of solvent is 0 to 90, preferably 40 to 70% by wt., based on the weight of components (a) to (d).

Non-aqueous acids and bases are used as condensation catalysts for non-aqueous precondensation. In particular, volatile acids such as halogen halides or glacial acetic acid which are optionally dissolved in one of the above-mentioned non-aqueous organic solvents, inorganic acids such as sulfuric acid, aluminum trichloride or boron trifluoride, or organic acids such as formic acid, acetic acid or propionic acid are suitable as acids. If alcoholic solutions of volatile acids are used such as methanolic 1N HCl, the total catalyst concentration may be e.g., up to 50 mole %, the addition taking place preferably in individual portions.

Inorganic and organic bases such as ammonia, sodium, potassium or calcium hydroxide, or trialkylamines are suitable as bases, volatile bases such as ammonia or trialkylamines being particularly preferred.

Precondensation is usually carried out at temperatures of —20° to 200° C., preferably 50° to 150° C. and particularly at the boiling point of the solvent.

Precondensation may also take place in different ways in the presence of water:

1) Partial hydrolysis:

Addition of less than stoichiometric water contents to the least reactive component. The more hydrolysis-reactive components are then added. The addition of water to component (a) may take place in various careful ways, e.g.
dissolved in alcohol,
addition of the water by means of a damp atmosphere,
production of the water in the reaction solution by ester formation, addition of salt hydrates.

2) Addition of hydrolysis-controlling compounds, e.g. 2,5-pentane dione, acetic acid, ethyl acetoacetate and the like, 3) Addition of agents that control drying, e.g., oxalic acid, formamide and the like.

If necessary, it is possible initially to precondense a part of one, several or all of the starting components, then to mix in the other starting components and subsequently co-condense them hydrolytically or non-hydrolytically.

Generally, precondensation is carried out until the resulting precondensate still has a liquid consistency.

The oligomer or low molecular weight, partially hydrolyzed and condensed inorganic-organic precondensate may then be isolated and dissolved in an organic solvent to a composition of defined viscosity. Higher alcohols, esters e.g., ethyl or amyl acetate, toluene, chloroform, acetone inter alia are suitable as solvent. The viscosity of the coating composition may be adjusted to a value in the region of 5 to 80 mPa.s which depends on the coating method chosen. The amount of solvent is generally 20 to 95, preferably 40 to 80% by wt., based on the weight of the precondensate.

Moreover, auxiliaries may be added, such as e.g.,

| fillers | 0–50% by wt. |
| viscosity regulators | 0–15% by wt. |
| preservatives | 0–2% by wt. |
| pigments | 0–2% by wt. |
| levelling and wetting agents | 0–5% by wt. |
| stabilizers | 0–5% by wt. |
| inhibitors | 0–5% by wt. |

(in each case based on the total weight of components (a) to (d)), which allow the consistency and colour of the mixtures to be adjusted individually.

The solutions obtained in this way are then applied to the dental materials or teeth to be coated by spraying, immersion or brushing. Immersion or brushing are preferred. After the solvent has evaporated, a multiple application may be appropriate.

A thermal after-treatment is subsequently carried out at temperatures between about 36° and 120° C. for a few minutes to a few hours, and the layer solidified. If organofunctional silanes with ethylenically unsaturated or epoxyfunctional groups are present, these may also be presolidified by cationic or radical polymerization before further polycondensation then takes place also at room temperature and over a relatively long period. In particular, it is possible, for the case of functional silanes with ethylenically unsaturated groups, to achieve a first solidification of the layers by radical polymerization, particularly by photopolymerization. To this end, cationic or radical initiators are added to the compositions. For example, aryl diazonium salts, diaryl iodonium salts, triaryl sulfonium salts and metallocene-like complex salts are suitable as cationic initiators. A preferred class of initiators for the purposes according to the invention are the metallocene complex salts known from EP-A 01 82 744, particularly the compound (I):

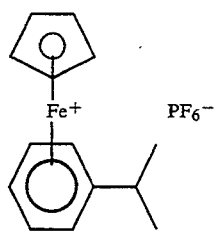
(I)

Another preferred class of initiators for cationic polymerization are the diaryl iodonium salts having the formula:

$$Ar_2I^+X^-,$$

in which Ar is an optionally substituted arene, for example benzene, toluene, xylene, ethyl benzene, methoxybenzene, naphthalene, 1,2-dihydronaphthalene, phenanthrene, anthracene, 9,10-dihydroanthracene, diphenylene, biphenyl, cumene; and in which $X^-$ is a complex anion, for example $BF_4^-$, $PF_6^-$, $AsF_6^-$, $SbF_6^-$, preferably $BF_4^-$ or $PF_6^-$. Diphenyl iodonium tetrafluoroborate, ditoluyl iodonium tetrafluoroborate, ditoluyl iodonium hexafluorophosphate and di-tert-butylphenyl iodonium tetrafluoroborate are particularly preferred. Other suitable diaryl iodonium salts are to be found for example in "UV Curing", Science and Technology, Ed. by S. Peter Pappas, Technology Marketing Corporation, Norwalk, USA, 06851 (1980).

Examples of suitable radical sources are organic peroxides e.g., diacyl peroxides such as benzoyl peroxide and lauroyl peroxide; ketoperoxides such as acetone peroxide and cyclohexanone peroxide, hydrocarbonperoxides such as tert-butyl hydroperoxide, cumene hydroperoxide and decahydronaphthalene hydroperoxide; dihydrocarbonperoxides such as di-tert-butyl peroxide and dicumyl peroxide; perketals such as 1,1-di-tert-butyl peroxy-3,3,5-trimethylcyclohexane; peresters such as tert-butyl perbenzoate, tert-butyl peroxyisopropyl percarbonate, tert-butyl perpivalate, tert-butyl peroctoate, tert-butyl cyclohexyl percarbonate, tert-butyl permaleinate, and acetylcyclohexane sulfonyl peroxide. Customary azo initiators such as azobisisobutyronitrile are also suitable.

All the photoinitiators known for curing light-curing plastics are suitable as photoinitiators. Suitable photoinitiators that initiate polymerization after irradiation by UV or visible light are, for example, benzoin alkylethers, benzil monoketals, acylphosphine oxides or aliphatic and aromatic 1,2-diketo compounds (for example camphor quinone).

So-called activators such as amines or organic phosphites may be added together with the photoinitiators in order to accelerate polymerization.

The material applied is exposed with the usual equipment. It is necessary merely to ensure that the light source is matched to the photoinitiator used i.e., that the wave length of the emitted light corresponds to the absorption behaviour of the photoinitiator. Mixtures of photoinitiators that cover a relatively wide absorption range make the process somewhat more dependent on the light source to be used in each case.

The initiators are used preferably in quantities of 0.05 to 3% by wt., based on the weight of the unsaturated compounds present in the compositions.

The cured coatings are resistant to plaque deposits. They are, moreover, characterized by homogeneous surfaces and do not impair the colour of the base material because of their transparency. They are scratch-proof and attrition resistant, resistant to hydrolysis and have a good surface hardness.

The coatings according to the invention are suitable for coating teeth and dental prostheses which, in the oral environment, are subject to the risk of plaque deposits. The coatings are particularly suitable for plastics materials such as prosthesis base plates, partial prostheses, false teeth, composite fillings, plastic inlays and, in particular, plastics veneers.

In a particular embodiment of the invention, the precondensates according to the invention may also be mixed with ethylenically unsaturated copolymerizable monomers which can be mixed homogeneously with the precondensate or are soluble therein. Suitable monomers are, for example, (meth)acrylic acid and salts thereof, preferably the alkali metal salts such as the sodium salt; (meth)acrylic esters such as methyl(meth)acrylate, ethyl(meth)acrylate, butyl(meth)acrylate, cyclohexyl(meth)acrylate, glycidyl(meth)acrylate, ethylene glycol mono(meth)acrylate, diethylene glycol mono(meth)acrylate, triethylene glycol mono(meth)acrylate, allyl(meth)acrylate, 2-hydroxypropyl(meth)acrylate, 3-hydroxypropyl(meth)acrylate; 2-ethoxyethyl(meth)acrylate, 2-dimethylaminoethyl(meth)acrylate and 3-methoxy-2-hydroxypropyl(meth)acrylate; (meth)acrylic amides such as (meth)acrylamide, N-methylol(meth)acrylamide and dimethyl(meth)acrylamide; allyl compounds such as allyl alcohol and allyl glycidyl ether; N-vinyl pyrrolidone, and styrene. Amongst said monomers, alkyl(meth)acrylates, alkoxyalkyl(meth)acrylates and hydroxyalkyl(meth)acrylates with 1 to 6 carbon atoms in the alkyl or alkoxy group, and N-vinyl pyrrolidone are particularly preferred. The amount of monomers may be 1 to 50% by wt., preferably 10 to 30% by wt., based on the total weight of precondensate and monomers.

If necessary, polymerization or copolymerization may be carried out in the presence of one or several unsaturated compounds as crosslinking agents. Special examples of suitable crosslinking agents are ethylene glycol di(meth)acrylate, diethylene glycol di(meth)acrylate, triethylene glycol di(meth)acrylate, butylene glycol di(meth)acrylate, neopentylglycol di(meth)acrylate, pentaerythritol tri(meth)acrylate, pentaerythritol tetra(meth)acrylate, allyl(meth)acrylate, trimethylol propane tri(meth)acrylate, divinyl benzene and diallyl phthalate.

Likewise suitable are the long-chain monomers according to U.S. Pat. No. 3,066,112 based on bisphenol-A and glycidyl methacrylate or their derivatives obtained by the addition of isocyanates. Compounds of the bisphenol-A-diethyl(meth)acrylate and bisphenol-A-dipropyl(meth)acrylate type are also suitable. The derivatives of the bisphenol-A types mentioned extended with alkoxyde units, for example, the diacrylic or dimethacrylic esters of bishydroxypolyalkoxy bisphenol-A derivatives are also suitable.

Moreover, the diacrylic and dimethacrylic esters of bishydroxymethyltricyclo[5.2.1.0$^{2,6}$] decane and of the derivatives extended with alkoxyde of bishydroxymethyltricyclo[5.2.1.0$^{2,6}$] decane mentioned in German patent 2 816 823 are also suitable. The reaction products of diisocyanates and hydroxyalkyl(meth)acrylates as described in the German patent specification 23 12 559 may also be used.

The amount of crosslinking agent is preferably 1 to 50 mole %, particularly 10 to 30 mole % based on the total molar number of monomers.

Depending on the choice of curing conditions, initiators of the above-mentioned kind are added to the monomers in the quantity ratios likewise mentioned. The application of the coatings and the curing thereof then takes place in a similar manner to that described above.

In a particular embodiment of the invention, mono or polyfunctional vinyl ethers and vinyl esters, for example, are suitable as cationically curing resins or cationically polymerizable monomers. Suitable vinyl ethers are trimethylol propane trivinyl ether, ethylene glycol divinyl ether and cyclic vinyl ethers. Triethylene glycol divinyl ether is particularly suitable.

The vinyl esters and vinyl ethers of polyfunctional alcohols are compounds that are generally highly suitable, polyethylene and polypropylene glycols with vinyl ether terminal groups being used in preference.

Cationically polymerizable heterocyclic compounds, for example, epoxides, are also highly suitable. In this case the glycidyl ethers of monohydric or polyhydric alcohols, for example the diglycidyl ethers of bisphenol-A are used in preference. The di- and polyepoxides of cycloaliphatic compounds, for example, the glycidyl ethers and β-methylglycidyl ethers of cycloaliphatic diols and polyols are particularly suitable for adjusting a high reactivity.

Glycidyl esters of carboxylic acids, particularly of di-and polycarboxylic acids, for example, the glycidyl esters of succinic acid, adipic acid, phthalic acid can also be used as glycidyl compounds.

Examples of particularly reactive glycidyl compounds are the diepoxides of vinylcyclohexane and dicyclopentadiene and 3-(3',4'-epoxycyclohexyl)-8,9-epoxy-2,4-dioxy-spiro-(5,5)-undecane and 3,4-epoxycyclohexylmethyl-3',4'-epoxycyclohexylcarboxylate.

Preferred epoxy resins are optionally pre-extended and/or pre-polymeric diglycidyl ethers of dihydric phenols or dihydric aliphatic alcohols with two to four C atoms. The pre-extended diglycidyl ethers of 2,2-bis-(4-hydroxyphenyl)propane are used in particular preference.

EXAMPLES OF PREPARATION

Example 1

13.68 g tetraethoxy titanate are dissolved in 50 ml of a mixture of toluene and ethanol (1:1), and 0.6 ml glacial acetic acid are added. This mixture is stirred for 0.5 h at 50° C. Separately from this, 30.28 g diphenylsilane diol are dissolved in a mixture of toluene and ethanol (1:1). This solution is added slowly dropwise to the tetraethoxy titanate solution with constant stirring at 50° C. and subsequently heated for 1 h at 75° C. under reflux conditions. A mixture of 10 ml water in 10 ml ethanol is added dropwise, with stirring, to the solution cooled to room temperature and the mixture stirred for 1 h at room temperature. Solvent and water are removed under reduced pressure at 60° C. A yellowish, transparent, viscous precondensate is obtained.

Example 2

13.8 g diphenyldichlorosilane are dissolved in 17.1 ml ethanol, 6.8 g methylvinyldichlorosilane are dissolved in 8.4 ml ethanol and 0.53 g tetraethoxysilane are dissolved in 1.5 ml ethanol. The ethanolic solutions are combined and heated for 2 h at 78° C. under reflux conditions. Then 7.2 ml 0.01N hydrochloric acid are added slowly dropwise at 70° C. and the preparation kept at this temperature for 0.5 h. The solvent and water are removed under a slight vacuum. The remaining silane is dissolved in acetic ester to a 10% solution and 0.2 g dibenzoyl peroxide are added. The coatings were dried at temperatures between 60° and 120° C.

Example 3

13.1 g diphenyldichlorosilane are dissolved in 15.8 ml ethanol, 6.5 g methylvinyl dichlorosilane are dissolved in 7.9 ml ethanol and 1.53 g tetraethoxysilane are dissolved in 3.0 ml ethanol. The solutions are combined and heated for 2 h at 78° C. under reflux conditions. 7.2 ml 0.01N hydrochloric acid are added slowly dropwise at 70° C. and the preparation is left at this temperature for 0.5 h. Solvent and water are distilled off under a slight vacuum. The silane is dissolved in acetic ester to a 10% solution. 0.2 g dibenzoyl peroxide were added to the coating solution. The coatings were dried at temperatures between 60° and 120° C.

Example 4

10.4 g methacryloxypropyl trimethoxysilane and 3.8 g methyltrimethoxysilane are mixed at room temperature and 5.75 g aluminum-sec-butylate are added dropwise with stirring. The mixture is stirred for 10 min and cooled to 15° C. 0.84 ml water are added slowly dropwise, stirred for 10 minutes and the solution cooled to 10° C. Afterwards, 1.68 ml water are added slowly dropwise and after 15 minutes' stirring a further 5 ml water are added. The product is stirred for 2 h. A clear solution is formed, from which the solvent is distilled off under a slight vacuum. The remaining product is dissolved in 50 ml acetic ester and the ester distilled off several times. Finally, a solution of the silane in 50 ml acetic ester is used for coatings. The layers are dried at 90° C.

Example 5

20 g tetraethoxysilane are dissolved in 50 ml ethanol and 0.6 ml glacial acetic acid are added. This mixture is stirred for 30 minutes at 50° C. and a solution of 26.2 g diphenylsilane diol in a mixture of toluene and ethanol (1:1) is added. This solution is added dropwise to the tetraethoxysilane solution with constant stirring at 50° C. and is heated subsequently for 1 hour at 75° C. under reflux conditions. A mixture of 10 ml water and 10 ml ethanol is added with stirring to this solution cooled to room temperature and stirred for 1 hour at room temperature. Solvent and water are removed under reduced pressure at 60° C. A colourless, transparent, viscous polymer is obtained which can be used for coating purposes.

EXAMPLES OF APPLICATION—PLAQUE DEPOSIT TESTS

Example 6

3.5 g of the precondensate of example 1 are dissolved in 6.5 g toluene. A thin layer is applied with a brush to the KOLLOCRYL B (PMMA) test specimen and dried for 24 h at 95° C. A glass-clear firmly adhering coating is obtained.

Example 7

The solution obtained in example 2 is brushed onto the test specimen and cured for 12 h at 80° C.

Example 8

0.1 g camphor quinone and 0.2 g 2-dimethylaminoethylmethacrylate are mixed with the solution obtained according to example 4. After the coating has been applied to the test specimens, it is dried for 10 minutes at 40° C. The layer is cured by 40 seconds' exposure with a commercial cold light apparatus (Elipar II, ESPE).

Principle of measurement:

Coated plastic test specimens were worn by patients for 3 days. The plaque accumulation was subsequently determined as a function of the coating method by weighing the test specimens.

Apparatus:

PMMA (test specimens made of prosthesis plastic KALLOCRYL B). Test specimen dimensions: $5 \times 7 \times 1$ mm Method:

The test specimens were coated according to the invention, dried to a constant weight in the drier and weighed using a precision balance. The test specimens were then inserted in an upper jaw mini plastic plate of three different subjects (1 female, 2 male, average age 21) and worn for 3 days in the mouth. The plates were not cleaned, only rinsed out roughly with water after meals. After the wearing time, the test specimens were removed from the support, dried for 24 hours in the drier and reweighed. Table 1 shows the plaque deposit as a function of the coating method in $\mu g/cm^2$.

Comparative Example 1

Uncoated test specimen

Comparative Example 2

Test specimen coated with conventional prosthesis sealant on an acrylate basis (Palaseal, Kulzer).

| Subject | Results: Plaque deposit [$\mu g/cm^2$] | | | | |
|---|---|---|---|---|---|
| | C1 | C2 | Ex. 6 | Ex. 7 | Ex. 8 |
| I | 1.94 | 1.74 | 0.47 | 0.68 | 0.42 |
| II | 1.87 | 1.68 | 0.31 | 0.55 | 0.38 |
| III | 1.98 | 1.81 | 0.53 | 0.48 | 0.78 |
| Average values | 1.93 | 1.74 | 0.44 | 0.57 | 0.54 |

The examples according to the invention show very substantially reduced plaque deposits in comparison with the uncoated test specimen (CI).

In contrast, a conventional surface seal based on an acrylate sealant does not exhibit any major reduction in plaque deposits compared with the uncoated test specimens. Moreover, the interesting effect emerged that the slight plaque deposits with the test specimens coated according to the invention could be removed very easily, whilst they adhered firmly to the comparative specimens.

In practice, this effect is particularly important because, in contrast to the state of the art, the residual deposits in the case of the coating according to the invention can be removed easily with a tooth brush.

I claim:

1. A method for coating teeth or dental prostheses, which comprises:

forming a composition which contains (a) at least on compound having Formula (I)

$$MR_x \qquad (I)$$

wherein M is selected from the group consisting of Ti, Zr, Si, Ge, Sn, and Al; R is selected from the group consisting of halogen, hydroxy, alkoxy, acyloxy and a chelate ligand; and x is a number corresponding to the valency of M; and either (b) an organic silane having Formula (II) or an oligomer thereof, or both, $$R''_n SiX_{4-n} \qquad (II)$$

wherein R'' is selected from the group consisting of alkyl, alkenyl, aryl, arylalkyl, alkylaryl, arylalkenyl, and alkenylaryl, each of which may be interrupted by oxygen atoms, sulfur atoms, or —NH— groups; X is selected from the group consisting of hydrogen, halogen, hydroxy, alkoxy, acyloxy, and the group —NR'$_2$, wherein each R' is hydrogen or alkyl, and n is 1, 2, or 3; or (c) an organofunctional silane having Formula (III) or an oligomer thereof, or both, $$R'''_m(R'''Y)_n SiX_{(4-m-n)} \qquad (III)$$

wherein R'', X and n have the meanings set forth above, R''' is selected from the group consisting of alkylene, phenylene, alkylenephenylene, and alkenylene, each of which may be interrupted by oxygen atoms, sulfur atoms, or —NH— groups; Y is selected from the group consisting of halogen, hydroxy, merapto, polyoxyalkylene, optionally substituted amino, quaternary ammonium, amido, polyamido, an aldehyde group, a keto group, a carboxy group, an alkoxycarbonyl group, a sulfonic acid group, a phosphoric acid group, an epoxy group, an acryloxy group, and a methacryloxy group, and m is 0, 1, or 2;

or a mixture of (b) and (c);

precondensing said composition to form a liquid precondensate;

adding a solvent and optionally at least one adjuvant to said precondensate to from a coating preparation;

applying said preparation to a tooth or dental prosthesis;

and curing said preparation.

2. The method of claim 1, wherein said polyoxyalkylene group is selected from the group consisting of glycyl and glyceryl.

3. The method of claim 1, wherein said composition comprises 1 to 99 mole % of component (a) and 1 to 99 mole % of component (b).

4. The method of claim 3, wherein said composition comprises 20 to 90 mole % of component (a) and 10 to 80 mole % of component (b).

5. The method of claim 4, wherein said composition comprises 40 to 80 mole % of component (a) and 20 to 60 mole % of component (b).

6. The method of claim 1, wherein said composition comprises 1 to 99 mole % of component (a) and 1 to 99 mole % of component (c).

7. The method of claim 6, wherein said composition comprises 20 to 90 mole % of component (a) and 10 to 80 mole % of component (c).

8. The method of claim 7, wherein said composition comprises 40 to 80 mole % of component (a) and 20 to 60 mole % of component (c).

9. The method of claim 1, wherein said composition comprises 1 to 98 mole % of component (a), 1 to 98 mole % of component (b), and 1 to 40 mole % of component (c).

10. The method of claim 9, wherein said composition comprises 20 to 80 mole %, of component (a), 10 to 75 mole % of component (b), and 5 to 30 mole % of component (c).

11. The method of claim 10, wherein said composition comprises 40 to 60 mole % of component (a), 15 to 50 mole % of component (b), and 10 to 25 mole % of component (c).

12. The method of claim 1, wherein said composition further comprises (d) a sparingly volatile oxide, soluble in said composition, of an element of Groups Ia to Va, or of Groups IVb or Vb of the Periodic Table, or a compound of said element that is soluble in said composition and which forms a sparingly volatile oxide, with the proviso that said element does not include titanium, zirconium, silicon, germanium, tin or aluminum.

13. The method of claim 12, wherein said composition contains 0.1 to 50% by weight of component (d) based on the total weight of components (a) to (d).

14. The method of claim 13, wherein said composition contains 0.5 to 30% by weight of component (d) based on the total weight of components (a) to (d).

15. The method of claim 14, wherein said composition contains 2 to 20% by weight of component (d) based on the total weight of components (a) to (d).

16. The method of claim 1, wherein said preparation is prepared by precondensing components (a), (b), (c) or a combination thereof in the desired quantity ratios optionally in the presence of a precondensation catalyst, isolating the resulting precondensate, and dissolving said precondensate in an organic solvent to obtain a preparation having a viscosity of about 5 to 80 mPa's.

17. The method of claim 12, wherein said preparation is prepared by precondensing components (a), (b), (c), (d) or a combination thereof in the desired quantity ratios, optionally in the presence of a precondensation catalyst, isolating the resulting precondensate, and dissolving said precondensate in an organic solvent to obtain a preparation having a viscosity of about 5 to 80 mPa's.

18. The method of claim 16, wherein said precondensate is mixed with an ethylenically unsaturated copolymerizable monomer, and optionally a crosslinking agent in a homogeneous mixture, and with an initiator.

19. The method of claim 17, wherein said precondensate is mixed with an ethylenically unsaturated copolymerizable monomer, and optionally a crosslinking agent in a homogeneous mixture, and with an initiator.

20. The method of claim 18, wherein said ethylenically unsaturated copolymerizable monomer, and optionally a crosslinking agent is present in an amount of 1 to 50% by weight, based on the total weight of precondensate and ethylenically unsaturated monomer/crosslinking agent, and wherein the quantity of said initiator is 0.05 to 3% by weight based on the weight of said ethylenically unsaturated monomer/crosslinking agent.

21. The method of claim 19, wherein said ethylenically unsaturated copolymerizable monomer, and optionally a crosslinking agent is present in an amount of 1 to 50% by weight, based on the total weight of precondensate and ethylenically unsaturated monomer/crosslinking agent, and wherein the quantity of said initiator is 0.05 to 3% by weight based on the weight of said ethylenically unsaturated monomer/crosslinking agent.

22. The method of claim 20, wherein the said ethylenically unsaturated copolymerizable monomer, and optionally a crosslinking agent is present in an amount of 10 to 30% by weight, based on the total weight of precondensate and ethylenically unsaturated monomer/crosslinking agent.

23. The method of claim 21, wherein said ethylenically unsaturated copolymerizable monomer, and optionally a wetting agent is present in an amount of 10 to 30% by weight, based on the total weight of precondensate and ethylenically unsaturated monomer/crosslinking agent.

24. The method of claim 16, wherein said curing is carried out at a temperature between room temperature and 120° C., optionally with irradiation with visible light or UV light.

25. The method of claim 23, wherein said curing is carried out at a temperature between room temperature and 120° C., optionally with irradiation with visible light or UV light.

26. The method of claim 24, wherein said preparation is applied to dental protheses made of plastic.

27. The method of claim 25, wherein said preparation is applied to dental protheses made of plastic.

28. The method of claim 26, wherein said preparation is applied to a plastic veneer.

29. The method of claim 27, wherein said preparation is applied to a plastic veneer.

30. The method of claim 12, wherein said sparingly volatile oxide is selected from the group consisting of $Li_2O$, $Na_2O$, $K_2O$, $CaO$, $MgO$, $As_2O_3$, $P_2O_5$, and $B_2O_3$.

* * * * *